US010065930B2

(12) United States Patent
Watanabe

(10) Patent No.: US 10,065,930 B2
(45) Date of Patent: Sep. 4, 2018

(54) METHOD FOR PRODUCING PYRIMIDINE-1-OL COMPOUND, AND INTERMEDIATE THEREOF

(71) Applicant: Eisai R&D Management Co., Ltd., Tokyo (JP)

(72) Inventor: Yuzo Watanabe, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/328,166

(22) PCT Filed: Aug. 3, 2015

(86) PCT No.: PCT/JP2015/071930
§ 371 (c)(1),
(2) Date: Jan. 23, 2017

(87) PCT Pub. No.: WO2016/021539
PCT Pub. Date: Feb. 11, 2016

(65) Prior Publication Data

US 2017/0204068 A1 Jul. 20, 2017

Related U.S. Application Data

(60) Provisional application No. 62/033,665, filed on Aug. 6, 2014.

(51) Int. Cl.
*C07D 239/34* (2006.01)

(52) U.S. Cl.
CPC .................................. *C07D 239/34* (2013.01)

(58) Field of Classification Search
CPC .............................. A01N 43/54; A61K 31/505
See application file for complete search history.

(56) References Cited

U.S. PATENT DOCUMENTS

| | | | | |
|---|---|---|---|---|
| 4,552,900 | A | 11/1985 | Sirrenberg et al. | |
| 5,117,064 | A | 5/1992 | Ito et al. | |
| 8,268,848 | B2 * | 9/2012 | Terauchi | C07D 401/12 514/269 |
| 2004/0229909 | A1 | 11/2004 | Kiyama et al. | |
| 2012/0095031 | A1 * | 4/2012 | Terauchi | C07D 401/12 514/269 |

FOREIGN PATENT DOCUMENTS

| | | |
|---|---|---|
| EP | 2 626 350 | 8/2013 |
| JP | A 59 184167 | 10/1984 |
| JP | A 61 069762 | 4/1986 |
| JP | A 62 292766 | 12/1987 |
| JP | A 62 292767 | 12/1987 |
| JP | A 03 220133 | 9/1991 |
| WO | WO 2003/016275 | 2/2003 |
| WO | WO 2008/069997 | 6/2008 |
| WO | WO 2012/039371 | 3/2012 |
| WO | WO 2013/123240 | 8/2013 |

OTHER PUBLICATIONS

International Search Report in International Application No. PCT/JP2015/071930, dated Oct. 27, 2015, 4 pages (with English Translation).
Lipinski, C.A. et al., "Bronchodilator and antiulcer phenoxypyrimidinones,"Journal of Medicinal Chemistry, 1980; 23:1026-1031 ISSN: 0022-2623.
Written Opinion in International Application No. PCT/JP2015/071930, dated Oct. 27, 2015, 4 pages (with English Translation).
Office Action issued in Japanese Application No. 2016-540213, dated Jun. 20, 2017, 6 pages, (with English translation).
Office Action issued in Israeli Application No. 250223, dated Feb. 6, 2018, 4 pages (with English translation).
Amendment and Written Appeal filed in JP Application No. 2016-540213, dated Nov. 22, 2017, English translation, 30 pages.
Wuts, Peter G.M. et al., "Protection for Phenols and Catechols," Greene 's Protective Groups in Organic Synthesis, Fourth Edition, 2007, pp. 367-430.
Response to Office Action in Japanese Application No. 2016-540213, dated Aug. 9, 2017, 18 pages (with English Translation).
Office Action issued in Japanese Application No. 2016-540213, dated Sep. 19, 2017, 6 pages (English Translation).
Greene, D.W., "Protection for Phenols and Catechols," *Protective Groups in Organic Synthesis*, Fourth Edition, Wiley, Chap. 3 (2007), pp. 367-430.
Notice of Allowance issued in Japanese Application No. 2016-540213, dated Jan. 9, 2018, 6 pages, with English translation.
Supplementary European Search Report issued in EP Application No. 15829152.6, dated Mar. 5, 2018, 5 pages.

* cited by examiner

*Primary Examiner* — Alexander R Pagano
*Assistant Examiner* — Ebenezer O Sackey
(74) *Attorney, Agent, or Firm* — Fish & Richardson P.C.

(57) ABSTRACT

There are provided a method for producing 2,4-disubstituted pyrimidine-5-ol, and particularly, 2,4-dimethylpyrimidine-5-ol and an intermediate thereof used in industrial production. The production method according to the present invention includes a step of producing 2,4-disubstituted pyrimidine-5-ol according to a hydrolysis reaction of a 2,4-disubstituted-5-(4-(nitrophenyl)oxy)pyrimidine compound and is suitable for industrial production since an inexpensive and easily available starting material can be used, regioselectivity of a substituent group is easily controlled, impurities are easily controlled, and 2,4-disubstituted pyrimidine-5-ol can be produced without using reagents and intermediates causing health problems, risks and the like.

7 Claims, No Drawings

METHOD FOR PRODUCING PYRIMIDINE-1-OL COMPOUND, AND INTERMEDIATE THEREOF

TECHNICAL FIELD

The present invention relates to a method for producing 2,4-disubstituted pyrimidine-5-ol which is a key intermediate for producing a compound that has an orexin receptor antagonistic action and is useful as an insomnia treatment agent and an intermediate for production thereof.

BACKGROUND

Two types of intracerebral neuropeptides, orexin-A (OX-A, a peptide consisting of 33 amino acids) and orexin-B (OX-B, a peptide consisting of 28 amino acids), expressed in neurons localized in the hypothalamus of the brain, were found as endogenous ligands (Patent Literature 5 and Non Patent Literature 1) of G protein-coupled receptors mainly existing in the brain, that is, orexin receptors (Patent Literature 1, Patent Literature 2, Patent Literature 3, and Patent Literature 4). It is known that the orexin receptors include two subtypes, an OX1 receptor (OX1) as a type 1 subtype and an OX2 receptor (OX2) as a type 2 subtype. OX1 more selectively binds to OX-A than to OX-B, and OX2 binds to OX-A similarly to OX-B. It was found that orexins stimulate food consumption in rats and physiological roles as mediators of such peptides in a central feedback mechanism to regulate feeding behaviors have been suggested (Non Patent Literature 1). On the other hand, it was observed that orexins also regulate states of sleep and wakefulness, and therefore orexins are considered to lead to a novel treatment method for narcolepsy as well as insomnia and other sleep disorders (Non Patent Literature 2). Further, it has been suggested that orexin signals in the ventral tegmental area associated with narcotic addiction and nicotine addiction play important roles in vivo in neuroplasticity (Non Patent Literature 3 and Non Patent Literature 4). In addition, it has been reported that, when OX2 is selectively inhibited in an experiment using rats, ethanol addiction is alleviated (Non Patent Literature 5). Moreover, it has been reported that the corticotrophin releasing factor (CRF) associated with depression and anxiety disorder in rats induces orexin-induced activity, and there is a possibility of orexins playing important roles in a stress response (Non Patent Literature 6).

5-chloro-2-{(5R)-5-methyl-4-[5-methyl-2-(2H-1,2,3-triazol-2-yl)benzoyl]-1,4-di azepan-1-yl}-1,3-benzoxazole (MK-4305; suvorexant, Patent Literature 6) having a dual orexin antagonistic action for OX1 and OX2 has recently been released as an insomnia therapeutic agent. Further, E2006 (Lemborexant) has been clinically developed.

In Patent Literature 7, a compound represented by the following formula or a pharmaceutically acceptable salt thereof is considerably described as a compound that has an orexin receptor antagonistic action and is expected to have an effect in insomnia treatment.

[Chem. 1]

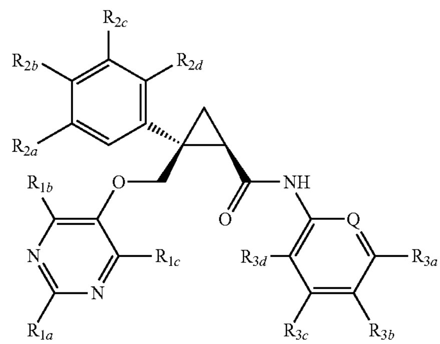

[In the formula, Q is —CH— or a nitrogen atom, $R_{1a}$ and $R_{1b}$ each independently represent, for example, a $C_{1-6}$ alkyl group, $R_{1c}$ represents a hydrogen atom, $R_{2a}$, $R_{2b}$, $R_{2c}$ and $R_{2d}$ each independently represent a hydrogen atom or a halogen atom, $R_{3a}$, $R_{3b}$ and $R_{3c}$ each independently represent a hydrogen atom or a halogen atom, and $R_{ad}$ represents a hydrogen atom.]

Among them, a compound represented by the following formula (A) that can be produced by the following method is reported in Patent Literature 8.

[Chem. 2]

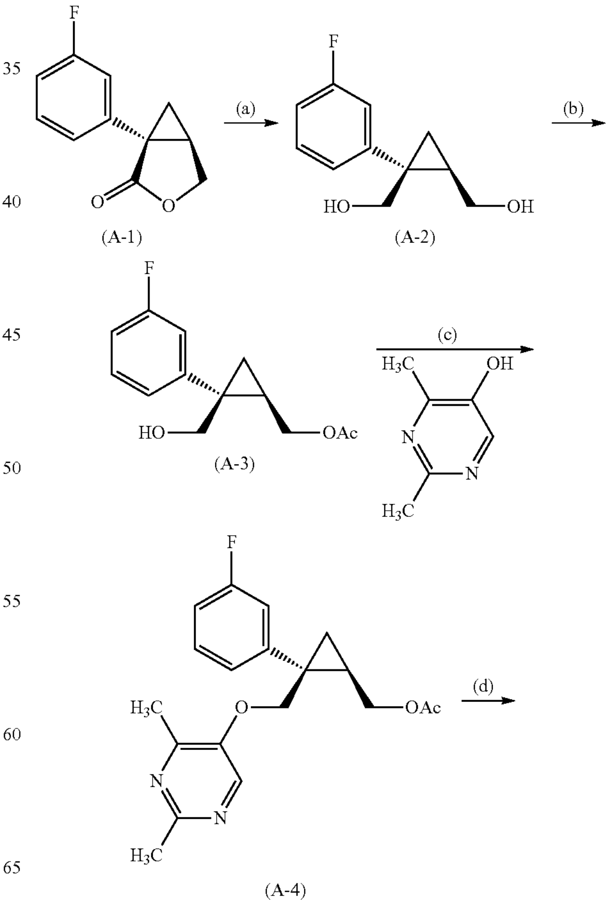

-continued

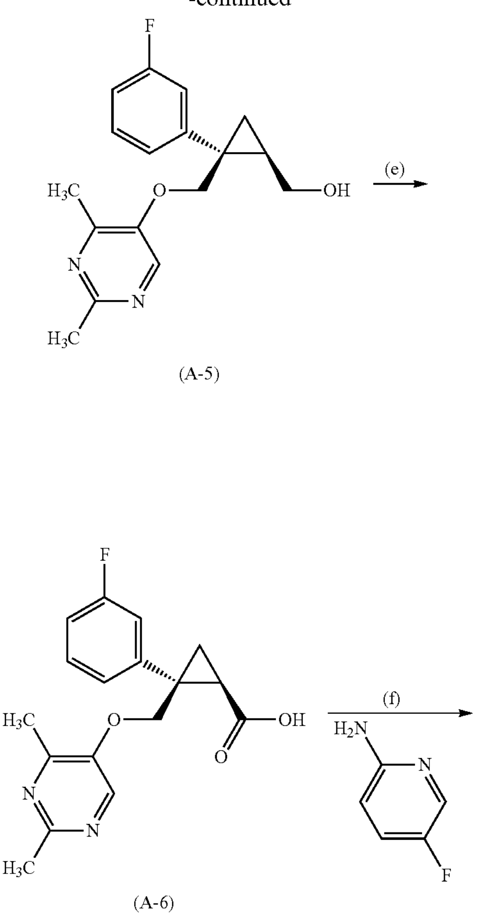

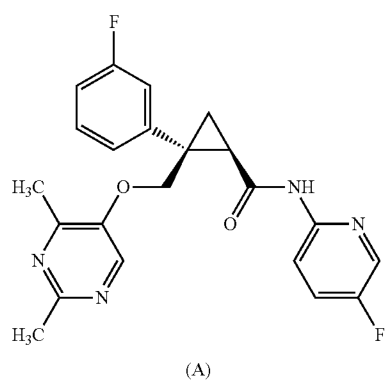 [SMILES: Cc1ncc(OC[C@@]2(c3cccc(F)c3)C[C@H]2C(=O)Nc2ccc(F)cn2)c(C)n1 ; "(A)"]

[In the formulae, Ac represents an acetyl group.]

(1R,2S)-2-{[(2,4-dimethylpyrimidin-5-yl)oxy]methyl}-2-(3-fluorophenyl)cyclopropylmethanol (A-5) produced in the above production method can be produced by reacting {(1R, 2S)-2-(3-fluorophenyl)-2-[(tosyloxy)methyl] cyclopropyl}methyl acetate produced from a compound (A-3) with 2,4-dimethylpyrimidine-5-ol (step (g)) and subsequent hydrolysis (step (d)) as shown in the following steps.

[Chem. 3]

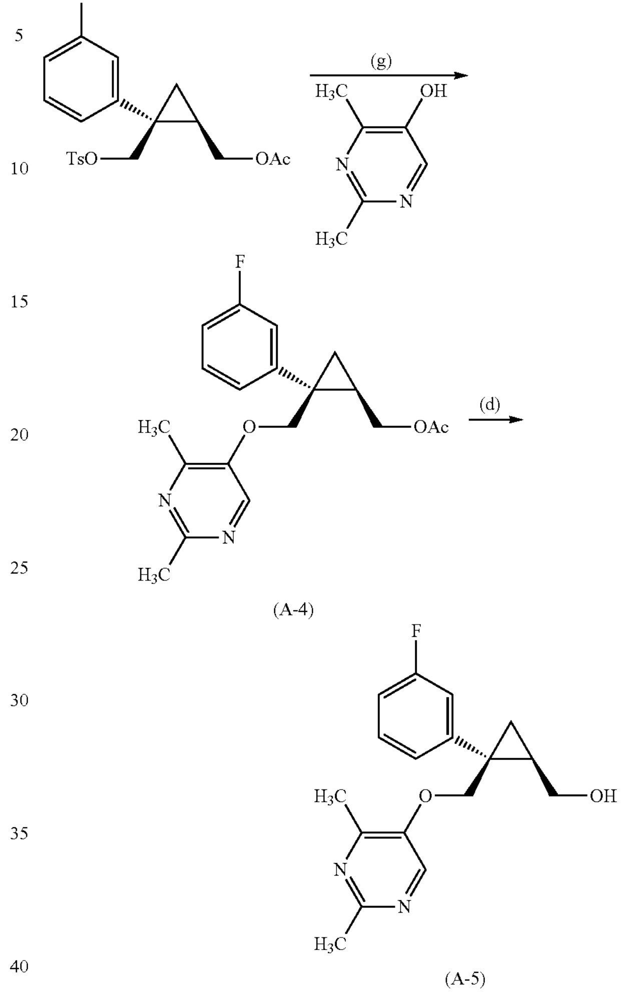

[In the formulae, Ac represents an acetyl group and Ts represents a p-toluenesulfonyl group.]

CITATION LIST

Patent Literature

[Patent Literature 1]
PCT International Publication No. WO 1996/34877
[Patent Literature 2]
Japanese Unexamined Patent Application, First Publication No. H10-327888
[Patent Literature 3]
Japanese Unexamined Patent Application, First Publication No. H10-327889
[Patent Literature 4]
Japanese Unexamined Patent Application, First Publication No. H11-178588
[Patent Literature 5]
Japanese Unexamined Patent Application, First Publication No. H10-229887
[Patent Literature 6]
PCT International Publication No. WO 2008/069997

[Patent Literature 7]

PCT International Publication No. WO 2012/039371

[Patent Literature 8]

PCT International Publication No. WO 2013/123240

Non Patent Literature

[Non Patent Literature 1]

Sakurai T. et al., Cell, 1998, 92, 573-585

[Non Patent Literature 2]

Chemelli R. M. et al., Cell, 1999, 98, 437-451

[Non Patent Literature 3]

S. L. Borgland et al., Neuron, 2006, 49, 589-601

[Non Patent Literature 4]

C. J. Winrow et al., Neuropharmacology, 2010, 58, 185-194

[Non Patent Literature 5]

J. R. Shoblock et al., Psychopharmacology, 2010, 215:191-203

[Non Patent Literature 6]

T. Ida et al., Biochemical and Biophysical Research Communications, 2000, 270, 318-323

DETAILED DESCRIPTION

In Production Example 4 in Patent Literature 7, a method for producing 2,4-dimethylpyrimidine-5-ol using 2,4-dichloro-5-methoxypyrimidine as a starting material is described.

[Chem. 4]

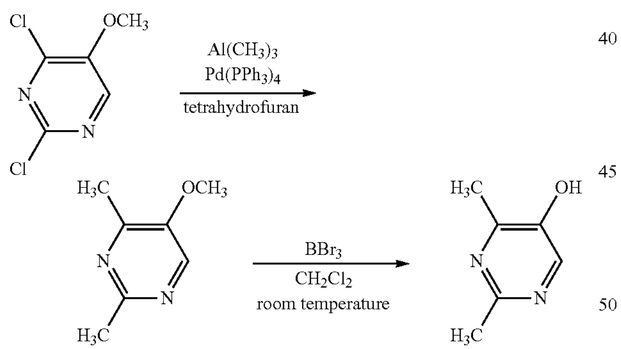

In the production method, 2,4-dichloro-5-methoxypyrimidine serving as a starting material is expensive, 2,4-dimethyl-5-methoxypyrimidine obtained as an intermediate is volatile, trimethyl aluminum used as a reagent causes health problems such as skin corrosiveness and irritation and has a risk of spontaneous ignition, and boron tribromide also causes health problems such as skin corrosiveness and irritation and requires careful handling. Therefore, the production method has problems when used in industrial production.

On pages 66 to 69 in Patent Literature 8, a method for producing 2,4-dimethylpyrimidine-5-ol using 2,4-dichloro-5-methoxypyrimidine as a starting material is described.

[Chem. 5]

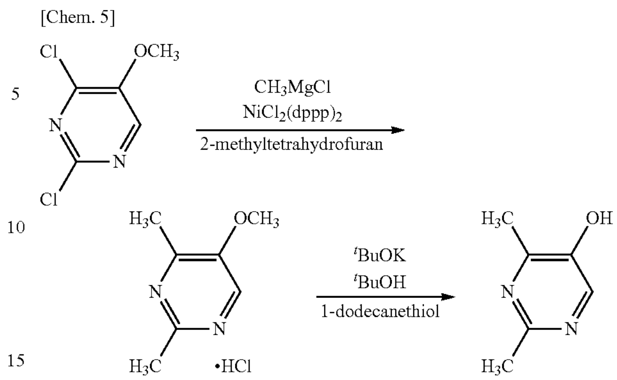

The production method also has problems such as expensive 2,4-dichloro-5-methoxypyrimidine is used as a starting material, and 2,4-dimethyl-5-methoxypyrimidine hydrochloride obtained as an intermediate has hygroscopicity. Further, in order for the production method to be used in industrial production, there are problems such as it is difficult to control impurities hydrogenated at the 2- or 4-position in methylation at the 2-position and 4-position of pyrimidine using methyl magnesium chloride.

Accordingly, an object of the present invention is to provide a method for producing 2,4-disubstituted pyrimidine-5-ol, and particularly, 2,4-dimethylpyrimidine-5-ol, used in industrial production.

The present invention includes the following aspects.

[1] A method for producing a compound of Formula (I) or a salt thereof

[Chem. 7]

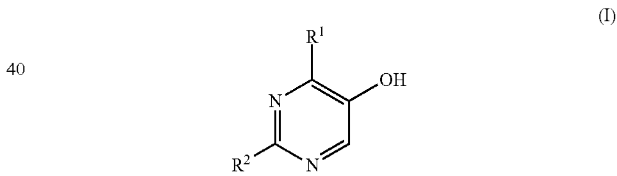

[In the formula, $R^1$ and $R^2$ represent $C_{1-6}$ alkyl groups that are same or different from each other.], comprising a step of hydrolyzing a compound of Formula (V) or a salt thereof.

[Chem. 6]

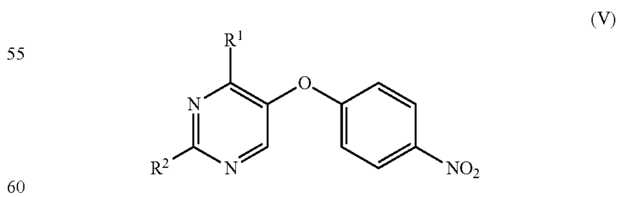

[In the formula, $R^1$ and $R^2$ represent $C_{1-6}$ alkyl groups that are the same or different from each other.]

[2] The production method according to [1], comprising a step of producing a compound of Formula (V) or a salt thereof by reacting a compound of Formula (IV) or a salt thereof with a compound of Formula (VI) or a salt thereof

[Chem. 10]

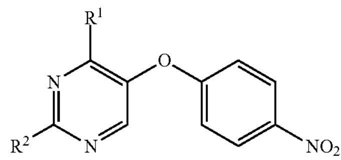

[In the formula, $R^1$ and $R^2$ represent $C_{1-6}$ alkyl groups that are the same or different from each other.]

[Chem. 8]

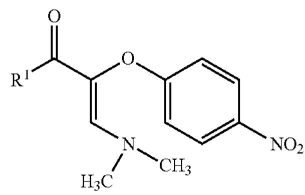

[In the formula, $R^1$ represents a $C_{1-6}$ alkyl group.]

[Chem. 9]

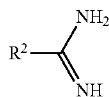

[In the formula, $R^2$ represents a $C_{1-6}$ alkyl group.]; and a step of hydrolyzing the compound of Formula (V) or the salt thereof.

[3] The production method according to [1], comprising a step of producing a compound of Formula (IV) or a salt thereof by reacting a compound of Formula (III) with N, N-dimethylformamide dimethyl acetal

[Chem. 12]

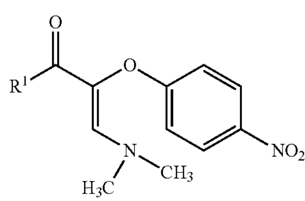

[In the formula, $R^1$ represents a $C_{1-6}$ alkyl group.]

[Chem. 11]

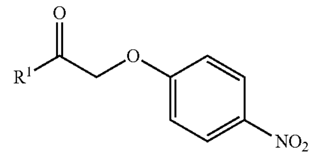

[In the formula, $R^1$ represents a $C_{1-6}$ alkyl group.];

a step of producing a compound of Formula (V) or a salt thereof by reacting a compound of Formula (IV) or a salt thereof with a compound of Formula (VI) or a salt thereof

[Chem. 14]

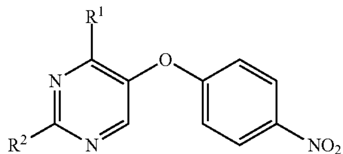

[In the formula, $R^1$ and $R^2$ represent $C_{1-6}$ alkyl groups that are the same or different from each other.]

[Chem. 13]

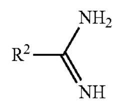

[In the formula, $R^2$ represents a $C_{1-6}$ alkyl group.]; and a step of hydrolyzing the compound of Formula (V) or the salt thereof.

[4] The production method according to [1], comprising a step of producing a compound of Formula (III) by reacting 4-nitrophenol with a compound of Formula (VII)

[Chem. 15]

(VII)

O $R^1$ X

[In the formula, X represents chlorine or bromine, and $R^1$ represents a $C_{1-6}$ alkyl group.]

[Chem. 16]

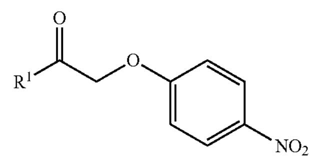

[In the formula, $R^1$ represents a $C_{1-6}$ alkyl group.];

a step of producing a compound of Formula (IV) or a salt thereof by reacting a compound of Formula (III) with N,N-dimethylformamide dimethyl acetal

[Chem. 17]

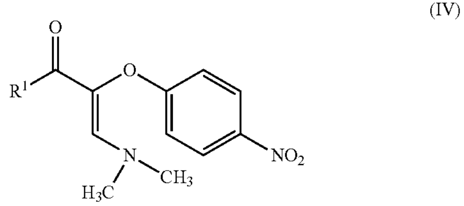

[In the formula, $R^1$ represents a $C_{1-6}$ alkyl group.];

a step of producing a compound of Formula (V) or a salt thereof by reacting the compound of Formula (IV) or the salt thereof with a compound of Formula (VI) or a salt thereof.

[Chem. 18]

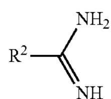

[In the formula, $R^2$ represents a $C_{1-6}$ alkyl group.]

[Chem. 19]

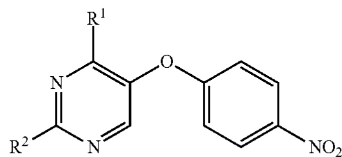

[In the formula, $R^1$ and $R^2$ represent $C_{1-6}$ alkyl groups that are the same or different from each other.]; and a step of hydrolyzing the compound of Formula (V) or the salt thereof.

[5] The production method according to any one of [1] to [4], wherein $R^1$ and $R^2$ are both methyl groups.

[6] A compound represented by Formula (V) or a salt thereof.

[Chem. 20]

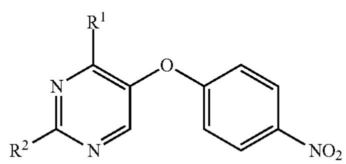

[In the formula, $R^1$ and $R^2$ represent $C_{1-6}$ alkyl groups that are the same or different from each other.]

[7] The compound or the salt thereof according to [6], wherein $R^1$ and $R^2$ are both methyl groups.

Advantageous Effects of Invention

The present invention provides a method for producing 2,4-disubstituted pyrimidine-5-ol which is an intermediate for producing a compound that has an orexin receptor antagonistic action and is useful as an insomnia treatment agent, and an intermediate thereof. In the production method of the present invention, an inexpensive and easily available starting material can be used, regioselectivity of a substituent group is easily controlled and impurities are easily controlled, and 2,4-disubstituted pyrimidine-5-ol can be produced without using reagents and intermediates causing health problems, risks and the like. Therefore, the production method is suitable for industrial production.

Hereinafter, the meanings of symbols, terms and the like described in this specification will be described and the present invention will be described in detail.

In this specification, structural formulae of compounds are not limited to formulae described for convenience, and may form salts. Further, crystal polymorphism may be present but it is not limited similarly, and any single crystalline form or a mixture thereof may be provided. A hydrate or a solvate other than an anhydride may be provided and all of them are included in the present invention.

In this specification, unless otherwise indicated, specific examples of a salt include hydrohalogenic acid salts (for example, hydrofluoride, hydrochloride, hydrobromide, and hydroiodide), and inorganic acid salts (for example, sulfate, nitrate, perchlorate, phosphate, carbonate, and bicarbonate).

The present invention includes an isotopically labeled compound of the compound described in this specification and a production method using the same. The isotopically labeled compound is the same as a compound described in the specification except that one or more atoms are replaced with atoms whose atomic mass and mass number are different from those normally found in nature. Isotopes that can be incorporated into the compound according to the present invention are isotopes of hydrogen, carbon, nitrogen, oxygen, and fluorine of the compound, and include $^2H$, $^3H$, $^{11}C$, $^{13}C$, $^{14}C$, $^{13}N$, $^{15}O$, and $^{18}F$.

The "$C_{1-6}$ alkyl group" in $R^1$ and $R^2$ represents a linear or branched alkyl group having 1 to 6 carbon atoms, and includes, for example, linear or branched alkyl groups such as a methyl group, an ethyl group, an n-propyl group, an isopropyl group, an n-butyl group, an isobutyl group, a t-butyl group, an n-pentyl group, an isopentyl group, a neopentyl group, an n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group, and a 3-methylpentyl group. As another aspect, a methyl group, an ethyl group, an n-propyl group, and the like are exemplified. As still another aspect, a methyl group is exemplified.

A method for producing 2,4-disubstituted pyrimidine-5-ol or a salt thereof according to the present invention includes a step of hydrolyzing a compound (V) or a salt thereof (fourth step; Step 4). In addition, as another aspect, a method for producing 2,4-disubstituted pyrimidine-5-ol according to the present invention includes a step (third step; Step 3) of producing a compound (V) or a salt thereof by reacting a compound (IV) or a salt thereof with an amidine derivative (VI) or a salt thereof in the presence of a base, and the fourth step. In addition, as still another aspect, a method for producing 2,4-disubstituted pyrimidine-5-ol or a salt thereof according to the present invention includes a step (second step; Step 2) of producing a compound (IV) or a salt thereof by a condensation reaction of N, N-dimethylformamide dimethyl acetal and a compound (III), the third step, and the fourth step. In addition, as yet another aspect, a method for producing 2,4-disubstituted pyrimidine-5-ol or a salt thereof according to the present invention includes a step (first step; Step 1) of producing a 4-nitrophenyloxymethyl ketone compound (III) by reacting a halomethylketone compound (VII) with 4-nitrophenol (II), the second step, the third step, and the fourth step.

[Chem. 21]

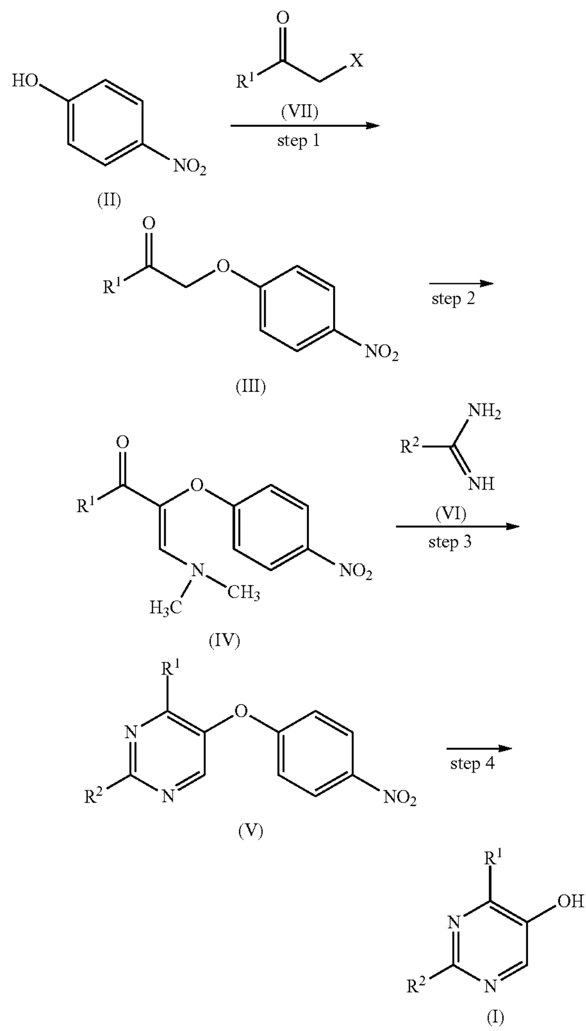

[In the formulae, $R^1$ and $R^2$ represent $C_{1-6}$ alkyl groups that are the same or different from each other.]

Hereinafter, these steps will be described in detail.

(First Step)

This step is a step of producing a 4-nitrophenyloxymethylketone compound (III) according to an alkylation reaction of a halomethyl ketone compound (VII) and a phenolic hydroxyl group of 4-nitrophenol (II).

Techniques that are well-known to those skilled in the art can be used for the alkylation reaction of the phenolic hydroxyl group. For example, the compound (VII) and the compound (II) are used in equivalent amounts or either thereof is used in a greater amount. A mixture thereof is stirred, in general, for 0.1 hour to 5 days, in the presence of a base, in a solvent inert to the reaction, in anywhere from a cooling range to a heating range, but preferably in a heating range. Exemplary solvents used here are not particularly limited, and include ketones such as acetone and methylethyl ketone, nitriles such as acetonitrile and propionitrile, aromatic hydrocarbons such as benzene, toluene, and xylene, halogenated hydrocarbons such as dichloromethane, 1,2-dichloro ethane, and chloroform, ethers such as diethyl ether, tetrahydrofuran, dioxane, and dimethoxyethane, aprotic polar solvents such as N,N-dimethylformamide, dimethyl sulfoxide, and N-methylpyrrolidone, and mixtures thereof. In addition, exemplary bases used here can include inorganic bases such as potassium carbonate, sodium carbonate, cesium carbonate, sodium hydrogen carbonate, sodium hydroxide, and potassium hydroxide, and organic bases such as triethylamine, diisopropylethylamine, and pyridine.

(Second Step)

This step is a step of producing a compound (IV) or a salt thereof according to a condensation reaction of a 4-nitrophenyloxy methyl ketone compound (III) and N, N-dimethylformamide dimethyl acetal.

Techniques that are well-known to those skilled in the art can be used for the condensation reaction. For example, the compound (III) and N, N-dimethylformamide dimethyl acetal are used in equivalent amounts or either thereof is used in a greater amount. A mixture thereof is stirred, in general, for 0.1 hours to 5 days, in a solvent inert to the reaction, in anywhere from a cooling range to a heating range, but preferably in a heating range. Exemplary solvents used here are not particularly limited, and include aromatic hydrocarbons, ethers, and mixtures thereof. Also, in order for the reaction to smoothly proceed, an acid of a catalytic amount may be added.

(Third Step)

This step is a step of producing a 2,4-disubstituted-5-(4-(nitrophenyl)oxy)pyrimidine compound (V) which is a compound of the present invention or a salt thereof according to a pyrimidine ring construction reaction of a compound (IV) or a salt thereof and an amidine derivative (VI) or a salt thereof.

Techniques that are well-known to those skilled in the art can be used for the pyrimidine ring construction reaction. For example, a compound (IV) or a salt thereof and a compound (VI) or a salt thereof are used in equivalent amounts or either thereof is used in a greater amount. A mixture thereof is stirred, in general, for 0.1 hour to 5 days, in the presence of a base, in a solvent inert to the reaction, in anywhere from a cooling range to a heating range, but preferably in a heating range. Exemplary solvents used here are not particularly limited, and include ketones, aromatic hydrocarbons, halogenated hydrocarbons, ethers, aprotic polar solvents, nitriles, and mixtures thereof. Also, an acid addition salt can be used as the amidine derivative. Exemplary bases used here can include inorganic bases such as potassium carbonate, sodium carbonate, cesium carbonate, sodium hydrogen carbonate, sodium hydroxide, and potassium hydroxide, and organic bases such as triethylamine, diisopropylethylamine, and pyridine.

(Fourth Step)

This step is a step of producing 2,4-disubstituted pyrimidine-5-ol or a salt thereof according to a hydrolysis reaction of a 2,4-disubstituted-5-(4-(nitrophenyl)oxy) pyrimidine compound (V) which is a compound of the present invention or a salt thereof.

Techniques that are well-known to those skilled in the art can be used for the hydrolysis reaction. For example, the compound (V) or the salt thereof, and equivalent amounts or a greater amount of base are used. A mixture thereof is stirred, in general, for 0.1 hours to 5 days, in a solvent inert to the reaction, in anywhere from a cooling range to a heating range, but preferably in a heating range. Exemplary solvents used here are not particularly limited, and include aromatic hydrocarbons, ethers, aprotic polar solvents, nitriles, alcohols such as methanol, ethanol, propanol, isopropanol, and butanol, water, and mixtures thereof. Exemplary bases used here can include inorganic bases such as potassium carbonate, sodium carbonate, cesium carbonate, sodium hydrogen carbonate, sodium hydroxide, potassium hydroxide, trisodium phosphate, and tripotassium phosphate, and organic bases such as triethylamine, diisopropylethylamine, and pyridine.

The production method according to the present invention has the following features.

(1) In the methods described in Patent Literature 7 and Patent Literature 8, expensive 2,4-dichloro-5-methoxypyrimidine is used as a starting material. However, in the production method according to the present invention, 2,4-disubstituted pyrimidine-5-ol can be produced using inexpensive and easily available 4-nitrophenol as a starting material.

(2) In the methods described in Patent Literature 7 and Patent Literature 8, it is difficult to control regioselectivity because trimethyl aluminum or methyl magnesium chloride is used to introduce a methyl group into dichloropyrimidine. However, in the production method according to the present invention, by appropriately selecting a reagent used as the compound (VI) or the compound (VII), any of $R^1$ and $R^2$ can be introduced, and thus regioselectivity is easily controlled and impurities are also easily controlled.

(3) 2,4-disubstituted pyrimidine-5-ol can be produced without using reagents and intermediates causing health problems such as skin corrosiveness and irritation, and having a risk of spontaneous ignition, volatility, and hygroscopicity and used in the methods disclosed in Patent Literature 7 and Patent Literature 8.

In addition, during condensation of N,N-dimethylformamide dimethyl acetal and the compound (III), a 4-nitrophenyl group assists regioselective condensation to provide the compound (IV), and additionally serves as a removable protecting group in relatively mild conditions in the fourth step.

EXAMPLES

Hereinafter, the present invention will be described in detail with reference to examples. However, the present invention is not limited to the following examples. In addition, abbreviations used below are conventional abbreviations well known to those skilled in the art and some abbreviations are as follows.

Chemical shifts in proton nuclear magnetic resonance ($^1$H-NMR) spectra were recorded in δ units (ppm) relative to tetramethylsilane and coupling constants were recorded in hertz (Hz). In patterns, s indicates singlet, d indicates doublet, br indicates broad, and m indicates multiplet.

$^1$H-NMR was measured using a JNM-AL400 nuclear magnetic resonance spectrometer (400 MHz) commercially available from JEOL.

In the following examples, the term "room temperature" indicates, in general, about 10° C. to about 35° C. Unless otherwise specified, % represents a weight percent.

Example 1

Production of 2,4-dimethylpyrimidine-5-ol

[Chem. 22]

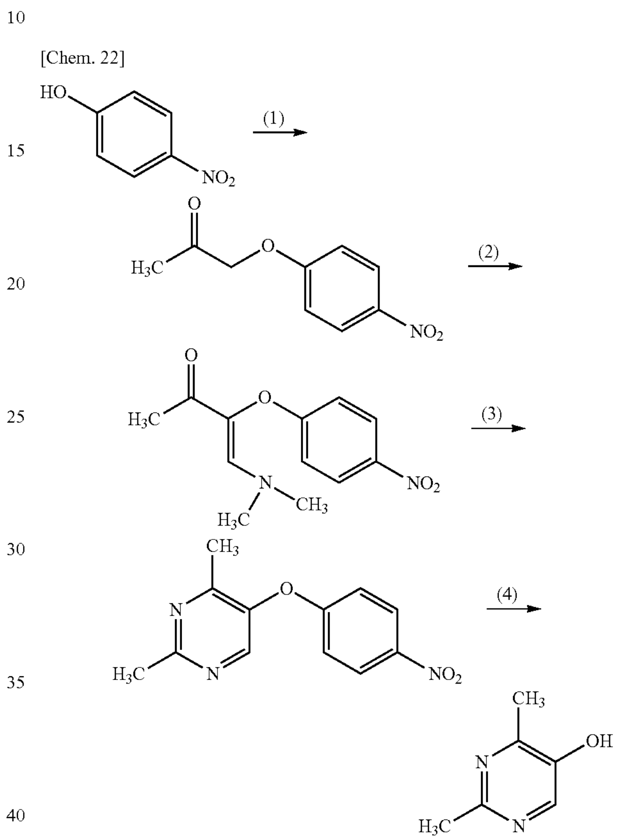

(1) Production of 1-(4-nitrophenoxy)propan-2-one

[Chem. 23]

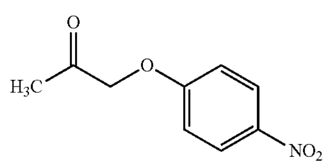

A mixture of 4-nitrophenol (10.0 g, 71.9 mmol), potassium carbonate (10.4 g, 75.5 mmol) and acetone (70 ml) was stirred for 30 minutes at 65° C. (external temperature). Chloroacetone (purity 96%, 6.3 ml, 75.5 mmol) was added dropwise to the reaction mixture at 65° C. (external temperature), and the obtained mixture was stirred for 9 hours at 65° C. (external temperature). The reaction mixture was cooled in an ice bath and water (120 ml) was then added dropwise to the reaction mixture at the same temperature. The reaction mixture was stirred for 1 hour at the same temperature and a precipitated solid was then filtered. The obtained solid was washed with water (100 ml) and dried under reduced pressure, and a target compound (10.9 g, 77%) was obtained.

$^1$H-NMR ($CD_3Cl$) δ (ppm): 2.31 (3H, s), 4.67 (2H, s), 6.95 (2H, d, J=9.3 Hz), 8.22 (2H, d, J=9.3 Hz)

(2) Production of (Z)-4-(dimethylamino)-3-(4-nitrophenoxy)but-3-en-2-one

[Chem. 24]

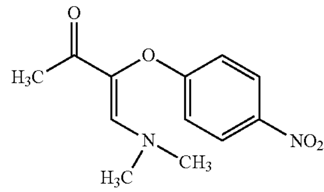

A mixture of 1-(4-nitrophenoxy)propan-2-one (4.20 g, 21.5 mmol), toluene (12.6 ml) and N, N-dimethylformamide dimethyl acetal (3.17 ml, 23.7 mmol) was stirred for 21 hours at 80° C. (external temperature). Toluene (8.4 ml) was added to the reaction mixture at the same temperature and stirred at room temperature. Additionally, the reaction mixture was stirred for 1 hour while cooling in an ice bath, and a precipitated solid was then filtered. The obtained solid was washed with toluene (4.2 ml) and then dried under reduced pressure, and a target compound (2.95 g, 55%) was obtained.

$^1$H-NMR ($CD_3Cl$) δ (ppm): 2.00 (3H, brs), 3.01 (6H, s), 6.90-7.16 (2H, brm), 7.16-7.46 (1H, brs), 8.22 (2H, d, J=8.8 Hz)

(3) Production of 2,4-dimethyl-5-(4-nitrophenoxy) pyrimidine

[Chem. 25]

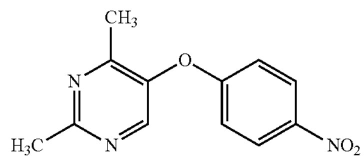

A mixture of (Z)-4-(dimethylamino)-3-(4-nitrophenoxy) but-3-en-2-one (3.00 g, 12.0 mmol), acetamidine hydrochloride (purity 96%, 1.42 g, 14.4 mmol), potassium carbonate (2.00 g, 14.4 mmol), and acetonitrile (30 ml) was stirred for 18 hours at 80° C. (external temperature), and then acetamidine hydrochloride (purity 96%, 1.42 g, 14.4 mmol) and potassium carbonate (2.00 g, 14.4 mmol) were added to the reaction mixture and stirred for 23 hours at 80° C. (external temperature). The reaction mixture was cooled in an ice bath and water (15 ml) and ethyl acetate (30 ml) were then added thereto. The obtained reaction mixture was stirred at room temperature, and organic layers were then separated, and washed with a 10% saline solution (6 ml). The obtained organic layers were dried using anhydrous sodium sulfate and a solvent was then evaporated under reduced pressure. The obtained residues were solidified using ethyl acetate-heptane (4.5 ml:9 ml) and filtered. The obtained solid was washed with ethyl acetate-heptane (1 ml:2 ml), and then dried under reduced pressure, and a target compound (2.51 g, 85%) was obtained.

$^1$H-NMR ($CD_3Cl$) δ (ppm): 2.40 (3H, s), 2.75 (3H, s), 6.96 (2H, d, J=9.0 Hz), 8.24 (2H, d, J=9.0 Hz), 8.32 (1H, s)

(4) Production of 2,4-dimethylpyrimidine-5-ol

[Chem. 26]

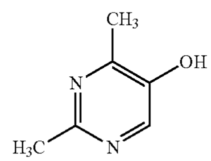

A mixture of 2,4-dimethyl-5-(4-nitrophenoxy) pyrimidine (2.50 g, 10.2 mmol), methanol (12.5 ml) and 48% aqueous sodium hydroxide (2.55 g, 30.6 mmol) was stirred for 20 hours at 60° C. (external temperature). The reaction mixture was cooled to room temperature and toluene (25 ml) and water (10 ml) were then added thereto. The obtained reaction mixture was stirred at room temperature, aqueous layers were then separated, and the aqueous layers were concentrated to an internal capacity of 12.5 ml under reduced pressure. Toluene (6.25 ml), concentrated hydrochloric acid (5.31 g, 51.0 mmol), and ethyl acetate (6.25 ml) were added to the obtained concentrated solution in an ice bath. The obtained reaction mixture was stirred at room temperature, and aqueous layers were then separated and washed with toluene-ethyl acetate (6.25 ml:6.25 ml). 2-methyltetrahydrofuran (25 ml) was added to the obtained aqueous layers, and 5 mol/l aqueous sodium hydroxide was then added in an ice bath to adjust a pH of 6-7. The obtained reaction mixture was stirred at room temperature, organic layers were then separated, and aqueous layers were reextracted with 2-methyltetrahydrofuran (25 ml). The obtained organic layers were combined and then washed with water (2.5 ml), and a solvent was evaporated under reduced pressure. Toluene (6.25 ml) was added to the obtained residues and suspended and stirred at 50° C. (external temperature). The mixture was stirred four 1.5 hours in an ice bath and then filtered. The obtained solid was washed with toluene (1.25 ml) and then dried under reduced pressure, and a target compound (1.16 g, 91%) was obtained.

$^1$H-NMR ($CD_3Cl$) δ (ppm): 2.51 (3H, s), 2.65 (3H, s), 8.03 (1H, s), 9.87 (1H, brs)

Example 2

Production of 2,4-dimethylpyrimidine-5-ol

[Chem. 27]

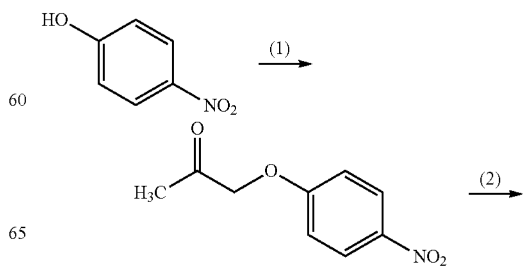

-continued

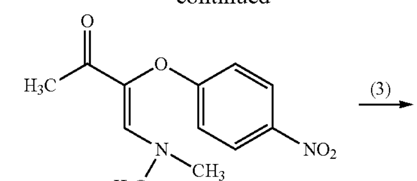

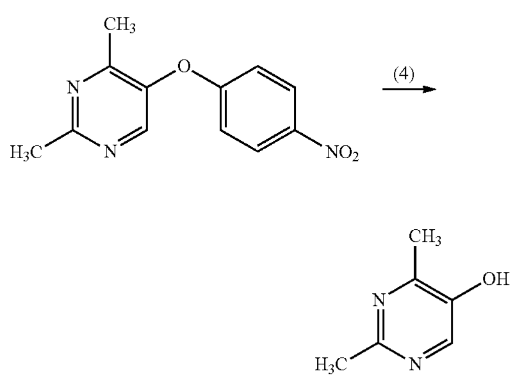

(1) Production of 1-(4-nitrophenoxy)propan-2-one

[Chem. 28]

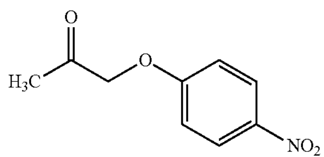

A mixture of 4-nitrophenol (100 g, 719 mmol), potassium carbonate (104 g, 755 mmol) and acetone (700 ml) was stirred for 45 minutes at 45° C. (external temperature). Chloroacetone (purity 96.3%, 72.5 g, 755 mmol) was added dropwise to the reaction mixture at 45° C. (external temperature), and the obtained mixture was stirred for 15 hours at 60° C. (external temperature). The reaction mixture was cooled in an ice bath and water (800 ml) and ethyl acetate (1000 ml) were then added thereto. The obtained reaction mixture was stirred at room temperature, organic layers were then separated, and 0.5 mol/l aqueous sodium hydroxide (500 ml), and sodium chloride (50 g) were added thereto. The obtained reaction mixture was stirred at room temperature, and organic layers were then separated, and washed with a 10% saline solution (500 ml). A solvent was evaporated under reduced pressure, the obtained residues were dissolved with toluene (500 ml) at 60° C. (external temperature), and then cooled to 5° C. (external temperature), and a precipitated solid was filtered. The obtained solid was washed with toluene (50 ml) and dried at 40° C. under reduced pressure, and a target compound (109 g, 78%) was then obtained.

$^1$H-NMR ($CD_3Cl$) δ (ppm): 2.31 (3H, s), 4.67 (2H, s), 6.95 (2H, d, J=9.3 Hz), 8.22 (2H, d, J=9.3 Hz)

(2) Production of (Z)-4-(dimethylamino)-3-(4-nitrophenoxy)but-3-en-2-one

[Chem. 29]

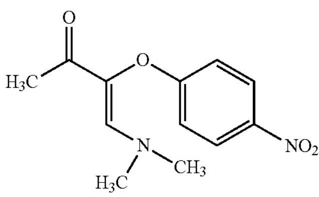

A mixture of 1-(4-nitrophenoxy)propan-2-one (109 g, 557 mmol), toluene (326 ml), and N, N-dimethylformamide dimethyl acetal (purity 98.3%, 82.9 ml, 613 mmol) was stirred for 21 hours at 80° C. (external temperature). Toluene (217 ml) was added to the reaction mixture at the same temperature and stirred at room temperature. Additionally, the reaction mixture was stirred for 1.5 hours while cooling in an ice bath, and a precipitated solid was then filtered. The obtained solid was washed with toluene (109 ml) and then dried under reduced pressure, and a target compound (57.0 g, 41%) was obtained.

$^1$H-NMR ($CD_3Cl$) δ (ppm): 2.00 (3H, brs), 3.01 (6H, s), 6.90-7.16 (2H, brm), 7.16-7.46 (1H, brs), 8.22 (2H, d, J=8.8 Hz)

(3) Production of 2,4-dimethyl-5-(4-nitrophenoxy)pyrimidine

[Chem. 30]

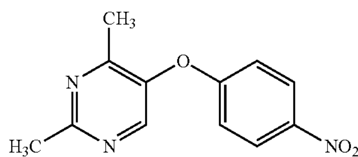

A mixture of (Z)-4-(dimethylamino)-3-(4-nitrophenoxy)but-3-en-2-one (56.8 g, 227 mmol), acetamidine hydrochloride (purity 96.7%, 53.3 g, 545 mmol), potassium carbonate (purity 99.5%, 75.7 g, 545 mmol), and acetonitrile (568 ml) was stirred for 20 hours at 80° C. (external temperature), and acetamidine hydrochloride (purity 96.7%, 2.22 g, 22.7 mmol) and potassium carbonate (purity 99.5%, 3.15 g, 22.7 mmol) were then added to the reaction mixture at 80° C. (external temperature) and stirred for 16 hours. The reaction mixture was cooled in an ice bath and water (568 ml) and ethyl acetate (568 ml) were then added thereto. The obtained reaction mixture was stirred at room temperature and organic layers were then separated and washed with a 10% saline solution (284 ml). A solvent was evaporated under reduced pressure, the obtained residues were dissolved with ethyl acetate (85.2 ml) at 60° C. (external temperature), and then cooled to room temperature, and heptane (170 ml) was added dropwise. The mixture was cooled in an ice bath and a precipitated solid was then filtered. The obtained solid was washed with ethyl acetate-heptane (18.9 ml:37.9 ml) and dried at 50° C. under reduced pressure, and a target compound (45.5 g, 82%) was obtained.

$^1$H-NMR ($CD_3Cl$) δ (ppm): 2.40 (3H, s), 2.75 (3H, s), 6.96 (2H, d, J=9.0 Hz), 8.24 (2H, d, J=9.0 Hz), 8.32 (1H, s)

(4) Production of 2,4-dimethylpyrimidine-5-ol

[Chem. 31]

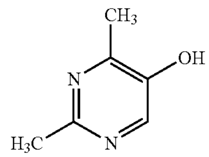

A mixture of 2,4-dimethyl-5-(4-nitrophenoxy) pyrimidine (39.8 g, 162 mmol), methanol (199 ml), and 48% aqueous sodium hydroxide (40.6 g, 487 mmol) was stirred for 18 hours at 60° C. (external temperature). The reaction mixture was cooled to room temperature and toluene (398 ml) and water (159 ml) were then added. The obtained reaction mixture was stirred at room temperature, aqueous layers were then separated and the aqueous layers were concentrated to an internal capacity of 199 ml under reduced pressure. Toluene (99.5 ml), concentrated hydrochloric acid (84.5 g, 811 mmol) and ethyl acetate (99.5 ml) were added to the obtained concentrated solution in an ice bath. The obtained reaction mixture was stirred at room temperature, and aqueous layers were then separated and washed with toluene-ethyl acetate (99.5 ml:99.5 ml). 2-methyltetrahydrofuran (398 ml) was added to the obtained aqueous layers and 5 mol/1 aqueous sodium hydroxide was then added in an ice bath to adjust a pH of 6-7. The obtained reaction mixture was stirred at room temperature, organic layers were then separated, and aqueous layers were reextracted with 2-methyltetrahydrofuran (398 ml). The obtained organic layers were combined and then washed with water (39.8 ml), and a solvent was evaporated under reduced pressure. Toluene (99.5 ml) was added to the obtained residues and suspended and stirred at 50° C. (external temperature). The mixture was stirred for 1.5 hours in an ice bath and then filtered. The obtained solid was washed with toluene (19.9 ml) and then dried under reduced pressure, and a target compound (18.8 g, 93%) was obtained.

$^1$H-NMR ($CD_3Cl$) δ (ppm): 2.51 (3H, s), 2.65 (3H, s), 8.02 (1H, s), 10.1 (1H, brs)

Example 3

Production of 2,4-dimethylpyrimidine-5-ol

[Chem. 32]

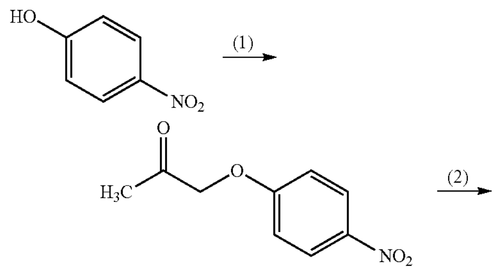

-continued

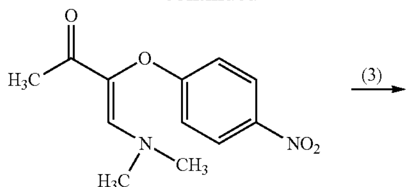

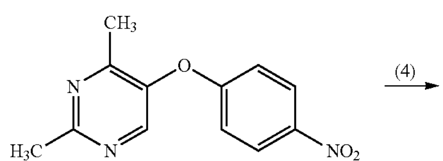

CH3 OH N H3C N (1) Production of 1-(4-nitrophenoxy)propan-2-one

[Chem. 33]

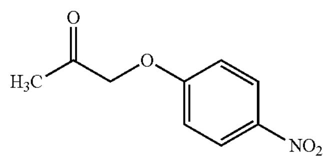

A mixture of 4-nitrophenol (10.0 g, 71.9 mmol), potassium carbonate (10.4 g, 75.5 mmol) and acetonitrile (70 ml) was stirred for 30 minutes at 60° C. (external temperature). Chloroacetone (purity 96.3%, 6.29 ml, 75.5 mmol) was added dropwise to the reaction mixture at 60° C. (external temperature), and the obtained mixture was stirred for 13.5 hours at 60° C. (external temperature). The reaction mixture was cooled in an ice bath and water (60 ml), and toluene (70 ml) were then added to the reaction mixture at the same temperature. The obtained reaction mixture was stirred at room temperature, and organic layers were then separated and washed with a 10% saline solution (50 ml). A solvent was evaporated under reduced pressure, the obtained residues were dissolved with toluene (50 ml) at 60° C. (external temperature), and then cooled in an ice bath, and a precipitated solid was filtered. The obtained solid was washed with toluene (5 ml) and dried under reduced pressure at 50° C., and a target compound (12.1 g, 86%) was then obtained.

$^1$H-NMR ($CD_3Cl$) δ (ppm): 2.31 (3H, s), 4.67 (2H, s), 6.95 (2H, d, J=9.3 Hz), 8.22 (2H, d, J=9.3 Hz)

(2) Production of (Z)-4-(dimethylamino)-3-(4-nitrophenoxy)but-3-en-2-one

[Chem. 34]

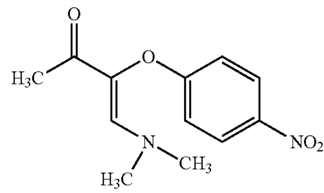

A mixture of 1-(4-nitrophenoxy)propan-2-one (12.1 g, 61.9 mmol), toluene (36.3 ml), and N, N-dimethylformamide dimethyl acetal (purity 98.3%, 9.22 ml, 68.1 mmol) was stirred for 21 hours at 80° C. (external temperature). Toluene (24.2 ml) was added to the reaction mixture at the same temperature and cooled to room temperature. Additionally, the reaction mixture was stirred for 2 hours while cooling in an ice bath and a precipitated solid was then filtered. The obtained solid was washed with toluene (12.1 ml), and then dried at room temperature under reduced pressure, and a crude form (7.76 g, 50%) of a target compound was obtained. Toluene-methanol (23.3 ml:3.88 ml) was added to the crude form (7.76 g) and suspended and stirred at 80° C. (external temperature), and toluene (15.5 ml) was added at the same temperature and cooled to room temperature. Additionally, the reaction mixture was stirred for 2 hours while cooling in an ice bath, and a precipitated solid was then filtered. The obtained solid was washed with toluene (7.76 ml) and then dried at room temperature under reduced pressure, and a target compound (5.90 g, 38%) was obtained.

$^{1}$H-NMR ($CD_3Cl$) δ (ppm): 2.00 (3H, brs), 3.01 (6H, s), 6.90-7.16 (2H, brm), 7.16-7.46 (1H, brs), 8.22 (2H, d, J=8.8 Hz)

(3) Production of 2,4-dimethyl-5-(4-nitrophenoxy) pyrimidine

[Chem. 35]

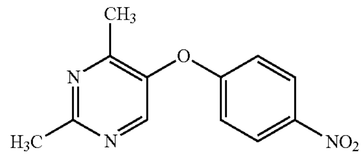

A mixture of (Z)-4-(dimethylamino)-3-(4-nitrophenoxy) but-3-en-2-one (3.00 g, 12.0 mmol), acetamidine hydrochloride (purity 96%, 2.83 g, 28.8 mmol), tripotassium phosphate (purity 98%, 6.23 g, 28.8 mmol) and acetonitrile (21.0 ml) was stirred for 22 hours at 80° C. (external temperature). The reaction mixture was cooled in an ice bath and water (18.0 ml) and ethyl acetate (21.0 ml) were then added thereto. The obtained reaction mixture was stirred at room temperature and organic layers were then separated and washed with a 10% saline solution (15 ml). A solvent was evaporated under reduced pressure, the obtained residues were dissolved with methanol (15.0 ml) at 50° C. (external temperature), and then cooled in an ice bath, and water (45.0 ml) was added dropwise. The mixture was stirred for 2 hours in an ice bath, and a precipitated solid was then filtered. The obtained solid was washed with water (6.00 ml), and then dried at room temperature under reduced pressure, and a target compound (2.78 g, 95%) was obtained.

$^{1}$H-NMR ($CD_3Cl$) δ (ppm): 2.40 (3H, s), 2.75 (3H, s), 6.96 (2H, d, J=9.0 Hz), 8.24 (2H, d, J=9.0 Hz), 8.32 (1H, s)

(4) Production of 2,4-dimethylpyrimidine-5-ol

[Chem. 36]

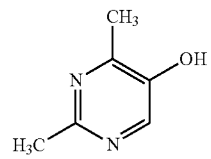

A mixture of 2,4-dimethyl-5-(4-nitrophenoxy) pyrimidine (3.58 g, 14.6 mmol), methanol (17.9 ml) and 48% aqueous sodium hydroxide (3.65 g, 43.8 mmol) was stirred for 19 hours at 60° C. (external temperature). The reaction mixture was cooled to room temperature, and toluene (35.8 ml) and water (14.3 ml) were then added thereto. The obtained reaction mixture was stirred at room temperature, and aqueous layers were then separated and the aqueous layers were concentrated to an internal capacity of 17.9 ml under reduced pressure. Toluene (8.95 ml), concentrated hydrochloric acid (7.60 g, 73.0 mmol), and ethyl acetate (8.95 ml) were added to the obtained concentrated solution in an ice bath. The obtained reaction mixture was stirred at room temperature, and aqueous layers were then separated and washed with toluene-ethyl acetate (8.95 ml:8.95 ml). Ethyl acetate (35.8 ml) was added to the obtained aqueous layers, and 5 mol/l aqueous sodium hydroxide was added in an ice bath to adjust a pH of 6-7. The obtained reaction mixture was stirred at room temperature, and organic layers were then separated and aqueous layers were reextracted with ethyl acetate (35.8 ml). The obtained organic layers were combined and then washed with water (1.07 ml), and a solvent was evaporated under reduced pressure. Toluene (8.95 ml) was added to the obtained residues and suspended and stirred at 50° C. (external temperature). The mixture was stirred for 2 hours in an ice bath and then filtered. The obtained solid was washed with toluene (1.79 ml) and then dried at 50° C. under reduced pressure, and a target compound (1.67 g, 92%) was obtained.

$^{1}$H-NMR ($CD_3Cl$) δ (ppm): 2.51 (3H, s), 2.65 (3H, s), 8.02 (1H, s), 10.01 (1H, brs)

INDUSTRIAL APPLICABILITY

The present invention provides a method for producing 2,4-disubstituted pyrimidine-5-ol which is an intermediate for producing a compound that has an orexin receptor antagonistic action and is useful as an insomnia treatment agent, and an intermediate thereof. In the production method of the present invention, an inexpensive and easily available starting material can be used, regioselectivity of a substituent group is easily controlled and impurities are easily controlled, and 2,4-disubstituted pyrimidine-5-ol can be produced without using reagents and intermediates causing health problems, risks and the like. Therefore, the production method is suitable for industrial production.

The invention claimed is:

1. A method for producing a compound of Formula (I) or a salt thereof, (I)

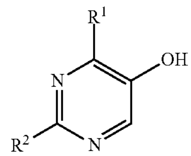

wherein in Formula (I), $R^1$ and $R^2$ represent $C_{1-6}$ alkyl groups that are the same or different from each other, comprising a step of hydrolyzing a compound of Formula (V) or a salt thereof (V)

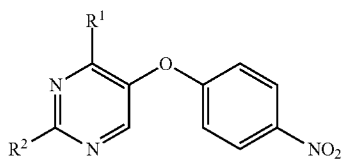

wherein in Formula (V), $R^1$ and $R^2$ represent $C_{1-6}$ alkyl groups that are the same or different from each other.

2. The production method according to claim 1, comprising a step of producing a compound of Formula (V) or a salt thereof by reacting a compound of Formula (IV) or a salt thereof with a compound of Formula (VI) or a salt thereof, (V)

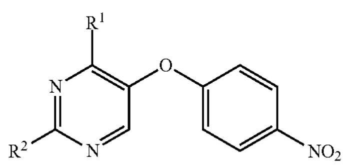

wherein in Formula (V), $R^1$ and $R^2$ represent $C_{1-6}$ alkyl groups that are the same or different from each other, (IV)

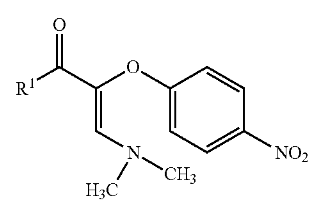

wherein in Formula (IV), $R^1$ represents a $C_{1-6}$ alkyl group, (VI)

wherein in Formula (VI), $R^1$ represents a $C_{1-6}$ alkyl group; and a step of hydrolyzing the compound of Formula (V) or the salt thereof.

3. The production method according to claim 1, comprising a step of producing a compound of Formula (IV) or a salt thereof by reacting a compound of Formula (III) with N, N-dimethylformamide dimethyl acetal, (IV)

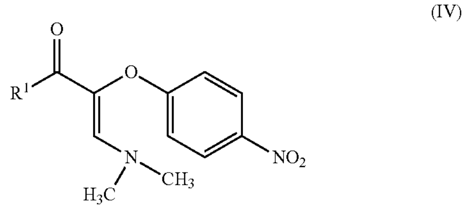

wherein in Formula (IV), $R^1$ represents a $C_{1-6}$ alkyl group, (III)

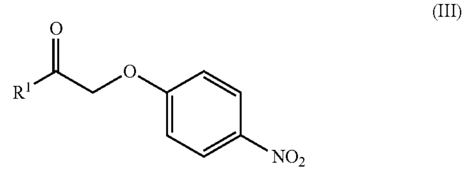

wherein in Formula (III), $R^1$ represents a $C_{1-6}$ alkyl group;

a step of producing a compound of Formula (V) or a salt thereof by reacting the compound of Formula (IV) or the salt thereof with a compound of Formula (VI) or a salt thereof, (V)

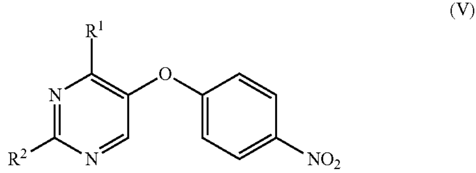

wherein in Formula (V), $R^1$ and $R^2$ represent $C_{1-6}$ alkyl groups that are the same or different from each other, (VI)

wherein in Formula (VI), $R^2$ represents a $C_{1-6}$ alkyl group; and a step of hydrolyzing the compound of Formula (V) or the salt thereof.

4. The production method according to claim 1, comprising a step of producing a compound of Formula (III) by reacting 4-nitrophenol with a compound of Formula (VII)

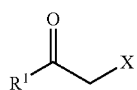

wherein in Formula (VII), X represents chlorine or bromine, and $R^1$ represents a $C_{1-6}$ alkyl group,

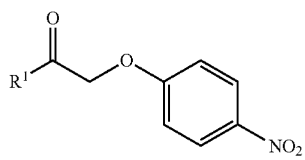

wherein in Formula (III), $R^1$ represents a $C_{1-6}$ alkyl group;

a step of producing a compound of Formula (IV) or a salt thereof by reacting the compound of Formula (III) with N,N-dimethylformamide dimethyl acetal,

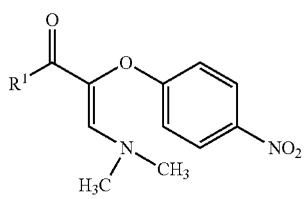

wherein in Formula (IV), $R^1$ represents a $C_{1-6}$ alkyl group;

a step of producing a compound of Formula (V) or a salt thereof by reacting the compound of Formula (IV) or the salt thereof with a compound of Formula (VI) or a salt thereof,

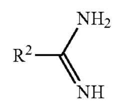

wherein in Formula (VI), $R^1$ represents a $C_{1-6}$ alkyl group,

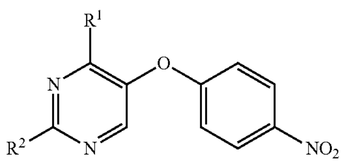

wherein in Formula (V), $R^1$ and $R^2$ represent $C_{1-6}$ alkyl groups that are the same or different from each other; and a step of hydrolyzing the compound of Formula (V) or the salt thereof.

5. The production method according to claim 1, wherein $R^1$ and $R^2$ are both methyl groups.

6. A compound represented by Formula (V) or a salt thereof,

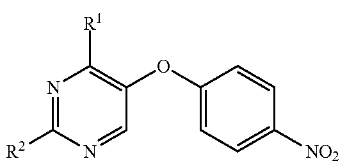

wherein in Formula (V), $R^1$ and $R^2$ represent $C_{1-6}$ alkyl groups that are the same or different from each other.

7. The compound or a salt thereof according to claim 6, wherein $R^1$ and $R^2$ are both methyl groups.

* * * * *

UNITED STATES PATENT AND TRADEMARK OFFICE

CERTIFICATE OF CORRECTION

PATENT NO. : 10,065,930 B2
APPLICATION NO. : 15/328166
DATED : September 4, 2018
INVENTOR(S) : Yuzo Watanabe It is certified that error appears in the above-identified patent and that said Letters Patent is hereby corrected as shown below:

In the Specification

Column 1
Line 56, delete "di azepan" and insert -- diazepan --.

Column 2
Line 24, delete "$R_{ad}$" and insert -- $R_{3d}$ --.

Column 3
Line 63, delete "{(1R, 2S)" and insert -- {(1R,2S) --.

Column 6
Line 47, delete "other.]," and insert -- other] --.

Column 7
Line 45, delete "group.];" and insert -- group]; --.

Column 8
Line 12, delete "group.];" and insert -- group]; --.
Line 39, delete "group.];" and insert -- group]; --.
Line 67, delete "group.];" and insert -- group]; --.

Column 9
Line 17, delete "group.];" and insert -- group]; --.
Line 44, delete "other.];" and insert -- other]; --.
Lines 48-49, delete "[4],
wherein $R^1$ and $R^2$ are both methyl groups." and insert -- [4], wherein $R^1$ and $R^2$ are both methyl groups. --.

Signed and Sealed this
Tenth Day of December, 2019

Andrei Iancu
*Director of the United States Patent and Trademark Office*

Column 11
Line 3, delete “N, N-dimethylformamide” and insert -- N,N-dimethylformamide --.

Column 15
Line 5, delete “8.22 (2H, d, J=9.3 Hz)” and insert -- 8.22 (2H, d, J=9.3 Hz). --.
Line 35, delete “Hz)” and insert -- Hz). --.

Column 16
Line 5, delete “s)” and insert -- s). --.
Line 48, delete “brs)” and insert -- brs). --.

Column 17
Line 67, delete “8.22 (2H, d, J=9.3 Hz)” and insert -- 8.22 (2H, d, J=9.3 Hz). --.

Column 18
Line 28, delete “Hz)” and insert -- Hz). --.
Line 67, delete “s)” and insert -- s). --.

Column 19
Line 31, delete “mol/1” and insert -- mol/l --.
Line 46, delete “brs)” and insert -- brs). --.

Column 20
Line 67, delete “8.22 (2H, d, J=9.3 Hz)” and insert -- 8.22 (2H, d, J=9.3 Hz). --.

Column 21
Line 39, delete “Hz)” and insert -- Hz). --.

Column 22
Line 7, delete “s)” and insert -- s). --.
Line 52, delete “brs)” and insert -- brs). --.

In the Claims

Column 24
Claim 2, Line 8, delete “$R^1$” and insert -- $R^2$ --.
Claim 3, Line 16, delete “N, N-dimethylformamide” and insert -- N,N-dimethylformamide --.

Column 26
Claim 4, Line 8, delete “$R^1$” and insert -- $R^2$ --.